(12) United States Patent
Nagy et al.

(10) Patent No.: US 8,570,186 B2
(45) Date of Patent: Oct. 29, 2013

(54) WIRELESS SENSOR READER

(75) Inventors: Michael Nagy, Lawrenceville, GA (US); Harry D. Rowland, Plainfield, IL (US); Roger Dwight Watkins, Dunlap, IL (US); Balamurugan Sundaram, Dunlap, IL (US)

(73) Assignee: Endotronix, Inc., East Peoria, IL (US)

( * ) Notice: Subject to any disclaimer, the term of this patent is extended or adjusted under 35 U.S.C. 154(b) by 0 days.

(21) Appl. No.: 13/455,776

(22) Filed: Apr. 25, 2012

(65) Prior Publication Data

US 2012/0319862 A1 Dec. 20, 2012

Related U.S. Application Data

(63) Continuation-in-part of application No. 13/423,693, filed on Mar. 19, 2012.

(60) Provisional application No. 61/478,647, filed on Apr. 25, 2011.

(51) Int. Cl.
*H04Q 5/22* (2006.01)

(52) U.S. Cl.
USPC ............... 340/870.02; 340/10.1; 340/10.3; 340/10.4; 340/13.2; 340/13.25

(58) Field of Classification Search
USPC .............. 340/10.1, 10.3, 10.4, 13.25, 825.71, 340/870.02; 455/161; 375/373–376
See application file for complete search history.

(56) References Cited

U.S. PATENT DOCUMENTS

| | | | | |
|---|---|---|---|---|
| 4,531,526 | A * | 7/1985 | Genest | 600/300 |
| 4,651,089 | A * | 3/1987 | Haigh | 324/76.42 |
| 7,046,964 | B1 * | 5/2006 | Sullivan et al. | 455/67.11 |
| 7,190,937 | B1 * | 3/2007 | Sullivan et al. | 455/130 |
| 7,245,117 | B1 * | 7/2007 | Joy et al. | 324/76.53 |

* cited by examiner

*Primary Examiner* — Daniel Wu
*Assistant Examiner* — John Bamert
(74) *Attorney, Agent, or Firm* — McDonald Hopkins LLC

(57) ABSTRACT

A wireless sensor reader is provided to interface with a wireless sensor. The wireless sensor reader transmits an excitation pulse to cause the wireless sensor to generate a ring signal. The wireless sensor reader receives and amplifies the ring signal and sends the signal to a phase-locked loop. A voltage-controlled oscillator in the phase-locked loop locks onto the ring signal frequency and generates a count signal at a frequency related to the ring signal frequency. The voltage-controlled oscillator is placed into a hold mode where the control voltage is maintained constant to allow the count signal frequency to be determined. The reader uses an ambient reading or other information to select a subset of the possible ring signal frequencies, and tunes or adjusts its circuits and algorithms to focus on that subset.

59 Claims, 3 Drawing Sheets

WIRELESS SENSOR READER

CROSS-REFERENCE TO RELATED APPLICATIONS

This application is a continuation-in-part of U.S. patent application Ser. No. 13/423,693 entitled "WIRELESS SENSOR READER," filed on Mar. 19, 2012, and claims priority to Provisional Patent Application No. 61/478,647 entitled "WIRELESS SENSOR READER TUNING BASED ON AMBIENT CONDITION," filed on Apr. 25, 2011, each of which are hereby incorporated by reference in their entirety.

FIELD OF INVENTION

The present invention generally relates to an apparatus and device for measuring a wireless signal from a sensor.

BACKGROUND

Wireless sensor and reader systems may be designed to wirelessly monitor the status of a remote sensor. Some such wireless systems include a sensor that transduces a physical parameter into a signal frequency. A reader is then configured to receive and measure the frequency of the sensor signal.

FIG. 1 illustrates an example of an operational frequency bandwidth of a wireless sensor/reader system and the corresponding parameter. As shown, the corresponding parameter is pressure, however it will be appreciated that the concept described herein may apply to any transduced parameter. The exemplary frequency range of the illustrated wireless sensor is from 13 to 14 MHz, which corresponds to absolute pressures of 550-900 mmHg. In the example shown in FIG. 1, frequency is inversely proportional to pressure.

In wireless sensor/reader systems, the sensor may be stimulated by a transmit pulse from a reader, causing the sensor to emit a ring back or "ring" signal at its resonant frequency once that stimulus is removed. The reader may measure the frequency of the ring signal and use a calibration table or formula to determine the sensed pressure.

The ring signal, as received at the reader, may be low power and may decay very quickly, particularly if the distance between sensor and reader is great. This is a problem with all similar wireless sensor systems, whether the systems utilizes a transmit signal that is fixed or swept. Other types of wireless sensor systems, such as those based on grid-dip techniques, may require a relatively long time and many transmit cycles to identify the sensor's resonance frequency, especially when the possible range of resonance frequencies is large.

Some wireless reader/sensor system designs require a gauge pressure reading, meaning pressure relative to local atmospheric pressure. In such designs, however, the sensor is often located at a position where it cannot access atmospheric pressure and thus cannot directly deliver a gauge pressure reading. For example, a blood pressure sensor implanted in the pulmonary artery is not capable of directly accessing atmospheric pressure. To deal with certain medical conditions, clinicians typically wish to know the gauge pressure of the pulmonary artery across a range of 100 mmHg. However, the implanted sensor has no way of knowing what the local atmospheric pressure is. In other words, the implanted sensor is only capable of sensing absolute pressure.

One solution is to place an ambient pressure sensor in the reader. The reader then measures absolute pressure from the implanted sensor, as well as absolute atmospheric ambient pressure from its ambient pressure sensor, and subtracts the ambient pressure from the absolute pressure to obtain gauge pressure.

The example in FIG. 1 illustrates a pressure range between 550-900 mmHg absolute. Ambient pressures in the inhabited regions of earth typically range from 550-800 mmHg absolute. Thus, to measure 0-100 mmHg gage, a sensor's absolute range must go from 550 mmHg (lowest ambient 550 mmHg plus lowest gauge 0 mmHg) to 900 mmHg (highest ambient 850 mmHg plus highest gauge 100 mmHg).

Therefore, there is a need to measure the frequency of a weak signal where the signal's full scale range is wide, but where only a small subset of that full range is used for any individual measurement.

Regardless of the method used to determine the sensor signal frequency, various circuits within the reader must be adapted or tuned to capture the maximum amount of energy in the sensor signal without capturing unwanted energy from sources other than the sensor, such as natural or man-made noise. For example, the reader's receiver antenna and internal filters, such as analog or digital filters, may be tuned to a passband that passes any possible frequency at which the sensor might resonate and rejects all frequencies outside that passband. However, widening the passbands of antennas and filters can cause problems, including higher attenuation, lower signal-to-noise ratios, and increased susceptibility to unwanted interfering signals.

Fixed frequency systems have difficulty overcoming these problems. Some swept frequency systems may attempt to overcome the problems by constantly re-tuning the receivers and filters to match the instantaneous frequency being transmitted. This, however, usually requires significant additional circuitry and processing.

Therefore, an improved method and apparatus are needed.

SUMMARY

A reader device is provided to interface with a wireless sensor. The reader emits a short pulse of energy or a short burst of radio frequency energy to cause the wireless sensor to ring. Immediately after the transmission, the reader receives and amplifies the sensor signal, then sends the signal to a phase-locked loop ("PLL") that locks to the sensor ring frequency. Once the PLL has locked to the ring frequency, the PLL's voltage controlled oscillator ("VCO") is placed in a hold mode to maintain the VCO frequency at the locked frequency. The VCO frequency is counted to determine the sensor resonant frequency.

The reader may include a device, such as a second sensor, to determine a set of possible frequency values of the ring signal. The components of the reader device may be tuned to the set of possible frequency values that are identified.

BRIEF DESCRIPTION OF THE DRAWINGS

Objects and advantages together with the operation of the invention may be better understood by reference to the detailed description taken in connection with the following illustrations, wherein.

DETAILED DESCRIPTION

Figure 1:
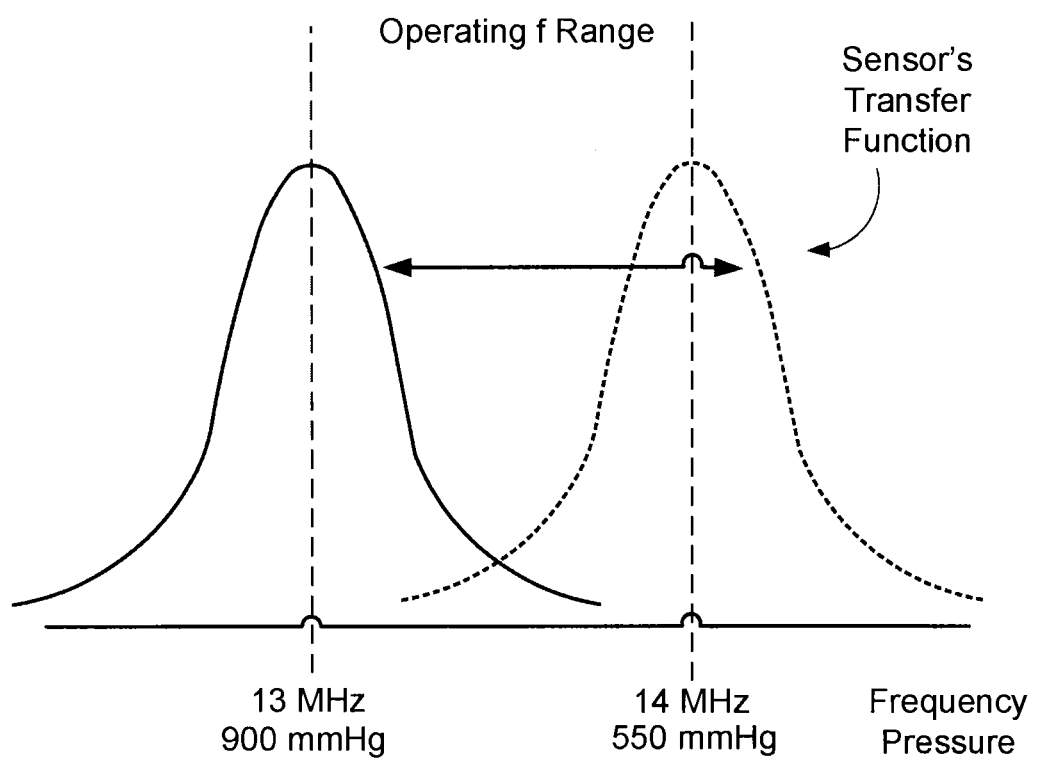
FIG. 1 is a graph of an operational frequency bandwidth of a sensor and corresponding parameter.
Figure 2:
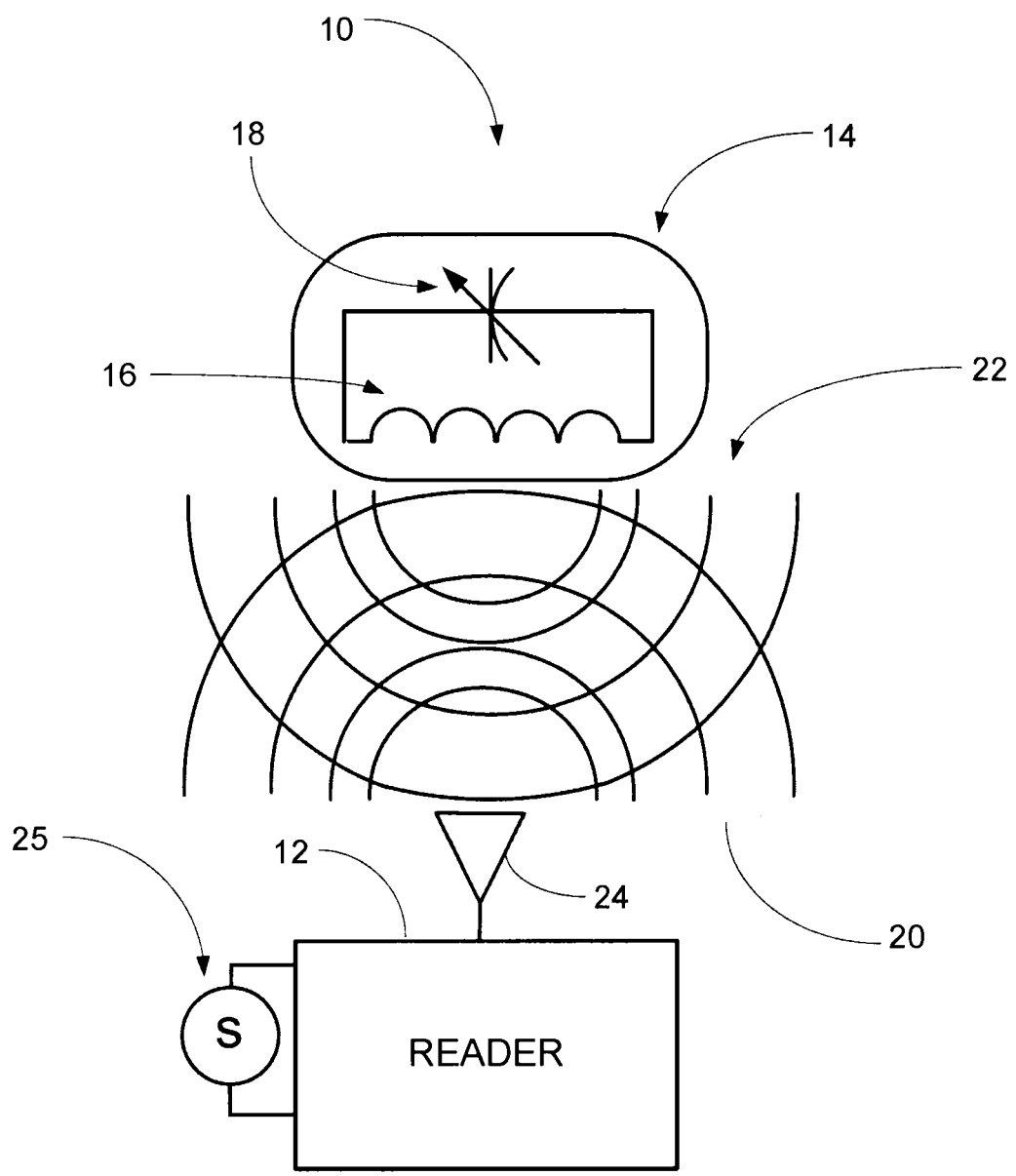
FIG. 2 is an embodiment of a wireless sensor system.

Reference will now be made in detail to exemplary embodiments of the present invention, examples of which are illustrated in the accompanying drawings. It is to be understood that other embodiments may be utilized and structural and functional changes may be made without departing from the respective scope of the present invention.

A wireless system 10 is generally provided. The wireless system 10 may include a wireless reader 12 and a wireless sensor 14. The wireless sensor 14 may be a passive device, such as a device comprising a capacitor 16 and an inductor 18, or an active device. The wireless sensor 14 may be implantable, such as implantable into a living being. For example, the wireless sensor 14 may be implanted in a human body to monitor a condition or parameter within the human body.

The reader 12 may be configured to transmit an excitation pulse 20 to excite the sensor 14. The excitation pulse 20 may cause the sensor 14 to ring or emit a ring signal 22 at its resonant frequency. The resonant frequency of the sensor 14 may vary based on a parameter sensed by the sensor 14. The reader 12 may measure the frequency of the ring signal 22 and determine the sensed parameter. For example, the reader 12 may utilize a formula, lookup table or calibration table to determine the sensed parameter.

The reader 12 may include a receiver to receive the ring signal 22 from the sensor 14. The receiver may comprise an antenna 24 or any other signal receiving device. The receiver may further include one or more filters, such as for example analog or digital filters, to filter the signal 22 received from the sensor 14. The filters may be tuned to a passband to allow a desired frequency bandwidth to be received by the reader 12. The passband may be narrowed to pass only a frequency band that corresponds to a specific parametric range of interest 26, shown in FIG. 3.

Exemplary embodiments described herein may make reference to monitoring and sensing a specific parameter, such as pressure. It will be appreciated, however, that the systems and methods set forth herein may be applied to any measured or sensed parameter, such as pressure, temperature, or any other parameter.

Figure 3:
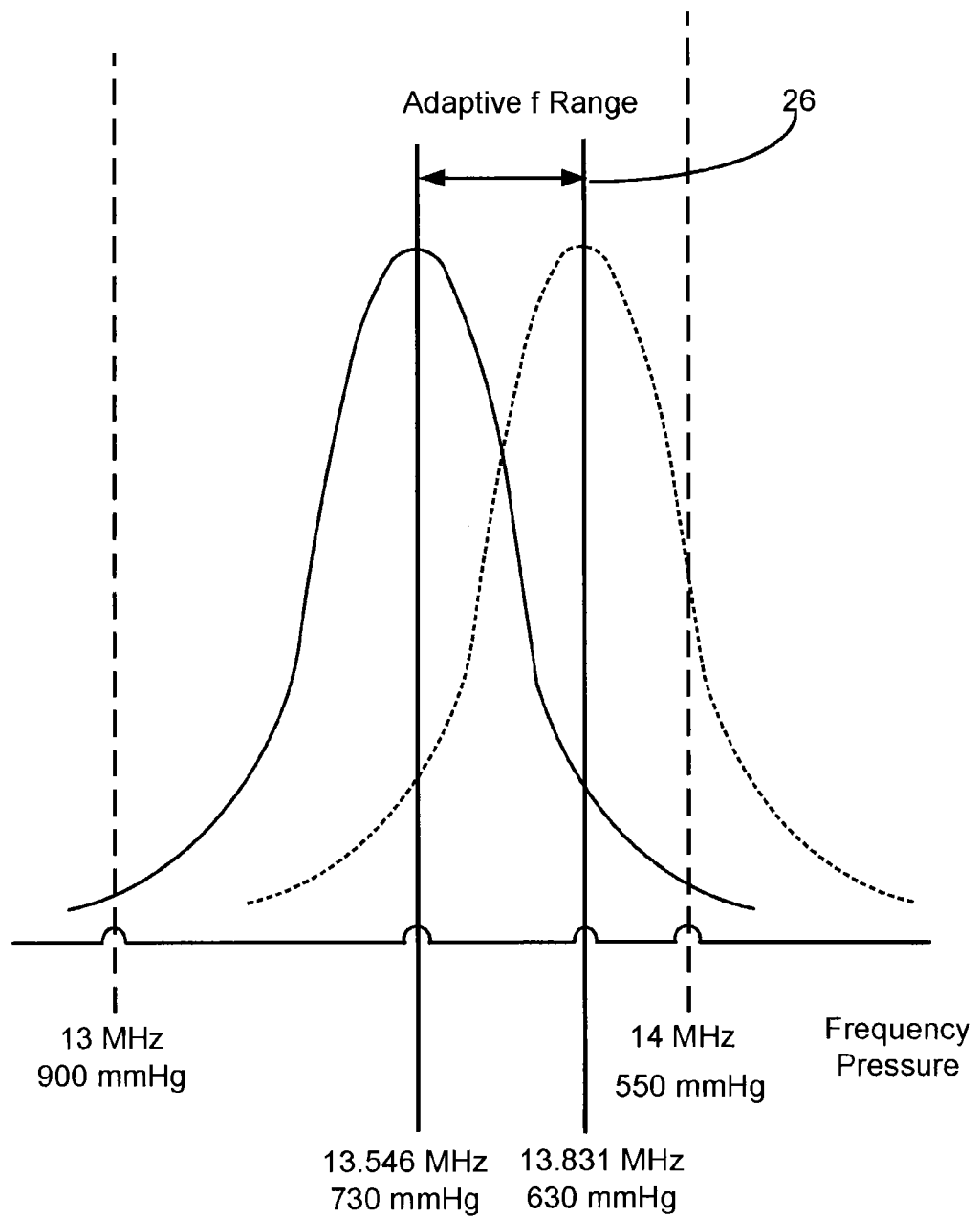
FIG. 3 is a graph of an operational frequency bandwidth of a sensor and corresponding parameter and bandpass window.

By way of a non-limiting example, a wireless system 10 adapted to sense a pressure, such as blood pressure, may include filters to narrow the passband window 26 to only receive frequencies that correspond to pressures within a 100 mmHg gauge pressure range. An example of this passband range 26 is illustrated in FIG. 3. The frequencies that correspond to pressures within a 100 mmHg gauge pressure range may be a "passband window" or "window of interest" 26 of the frequencies that provide the optimal or most valuable data. It will be appreciated, however, that the passband window 26 may correspond to any appropriate range of the sensed parameter.

The spectral location of the passband window 26 within the total range of absolute pressure may vary to capture the desired data. For example, the location of the window 26 may be determined based on the ambient pressure at the time the reader 12 is receiving the ring signal 22 from the sensor 14. To that end, the reader 12 may include an ambient sensor 25, such as an ambient pressure sensor, to sense an ambient condition, such as pressure. The ambient sensor 25 may be embedded in or located on the reader 12. The ambient sensor 25 may also be located away from the reader 12, such as part of another device or system that communicates its ambient reading to the reader 12 or to a third party processor, for determining the location of the passband window 26.

As shown in the graph illustrated in FIG. 3, the passband window 26 may be optimally located based on the ambient pressure measured by the reader's ambient pressure sensor 25. For example, in an embodiment where the sensor is a wireless pressure sensor implanted in the pulmonary artery of a human being, the pressure range of interest is 0-100 mmHg above ambient. Therefore, the Reader's processor would be programmed to locate a passband window 26 such that its edges are at frequencies corresponding to the ambient pressure reading, and a pressure that is 100 mmHg greater than the ambient pressure reading, as shown in FIG. 3. Accordingly, the reader 12 may tune its antenna 24, as well as its internal circuits and algorithms, to focus the passband window 26 near the ambient pressure.

In an embodiment, a wireless sensor 14 may be implanted into a human being located at relatively high altitude, for example an altitude having an ambient pressure near 630 mmHg absolute. The pressure range of interest may therefore be 630-730 mmHg absolute, corresponding to a frequency passband window 26 of 13.831-13.546 MHz. The reader 12 may measure the ambient pressure using its ambient pressure sensor 25. The reader 12 may then determine, from the ambient pressure measurement, the subset of the full-scale frequency range that will contain the remote sensor's frequency. The reader 12 may then tune its receiver, such as the antennas 24, filters, amplifiers, other circuits, or algorithms, to pass the desired subset and block the unwanted portion of the range. For example, the reader 12 may increase the Q of its receiving antenna by narrowing its bandwidth to match the frequency window 26. Additionally, the reader 12 may increase the gain and signal-to-noise ratio of one or more amplifiers in the receive chain by tuning them to the passband window 26. The reader 12 may also tune filters in the receive chain to match the passband window 26, and thus filter out any noise or interference outside the passband window 26. The reader 12 may take numerous pressure readings from the sensor and average them (in its own embedded processor or in a remote processor) to further improve accuracy. The averaging processor may implement an algorithm by which all readings that fall outside the passband window 26 are considered spurious outliers and are not included in the average.

This system and method, as described, provide several advantages over known systems and methods. For example, restricting the passband window 26 of the received ring signal 22 may allow a sensor 14 with a higher Q to be used, thus providing a longer decay time and higher ring signal 22 amplitude. Restricting the passband window 26 also allows for receiver antennas 24 and filters having a higher Q to be used, thus increasing signal to noise ratio. Further, in systems that utilize a fixed-frequency excitation pulse 20, the sensor's transfer function roll-off dictates that the ring signal 22 may be weaker when the sensor 14 is near the edges of its operational frequency range. Adapting the reader's circuitry to focus on bands near the edges may compensate for this effect.

Once the passband window 26 has been determined, many of the reader's internal components may be tuned to focus only on the range of the passband window 26. For example, the reader's receive antenna 24 may be tuned to the passband window 26 containing the ring signal 22. This may be accomplished by switching reactive components in and out of the antenna circuit, including parts of the antenna 24, or by other methods known in the art.

The wireless system 10 may include an amplifier section. The amplifier section may include filters and amplifiers. The filters and amplifiers may be adaptively tuned to the frequency passband window 26 that contains the ring signal 22. This can be accomplished by switching reactive components in and out of the amplifier and filter circuits, or by other methods known in the art.

The wireless system 10 may include at least one phase lock loop (PLL) to lock onto and help determine the ring frequency. The initial reference frequency for the PLL may be set to approximately the center of the frequency passband window 26. This will reduce the time it takes for the PLL to lock onto the ring signal 22 frequency. For example, the reader 12 processor may calculate or look up the control voltage of the PLL's voltage controlled oscillator (VCO) that corresponds to the center of the passband window 26, as defined by the reader's ambient pressure sensor 25. Other methods and circuits for locking and pre-locking the PLL may be used in conjunction with the systems and methods described herein. The PLL may lock the frequency of the ring signal. Additionally or alternatively, the PLL may hold the frequency of the ring signal constant for a length of time sufficient to ascertain the frequency of the ring signal.

The excitation pulse 20 emitted by the reader 12 may be held at an approximately fixed frequency. The fixed excitation pulse 20 may be adapted to be located near the center of the passband window 26 containing the ring signal 22. As a result, the system may utilize a sensor 14 having a higher Q that may provide a stronger, longer lasting ring signal 22.

The wireless system 10 may utilize a swept frequency excitation pulse 20. The bandwidth of the swept frequency excitation pulse 20 may be limited to the passband window 26 containing the ring signal 22. Limiting the excitation pulse 20 in this manner may reduce the time required to acquire the ring signal 22 and allow more samples to be taken for a given pressure instance.

The parameter measured by the sensor 14 may be static or quasi-static in comparison to the speed of measurement. By way of a non-limiting example, a measured blood pressure waveform may be static or quasi-static in comparison to the speed of measurement. In such circumstances, the reader 12 may take multiple readings of the sensor 14 measurement and average them using a processing algorithm. For example, as the ring signal 22 gets weaker and the signal-to-noise ratio (SNR) decreases, the number of noisy, spurious readings may increase. The reader 12 may be configured to ignore any measurements that lie outside the passband window 26 during the averaging process to remove outlying and inaccurate data.

The reader 12 may sample the incoming ring signal 22 and compare the input data with the passband window 26. Based on the comparison, the input data from the ring signal 22 may be stored or discarded. The reader 12 may also optimize or enhance processing of the signal, for example with FFT methods, by only processing portions of the signal that are within the allowed frequency band based on the filtered passband window 26. Other methods of improving the measurement of the received signal based on narrowing the allowed frequency band to match the ambient measurement may also be utilized.

The examples used herein are directed to an ambient pressure reading to determine a narrowed bandwidth for the absolute reading and adapt the reader 12 circuitry and/or algorithms to that bandwidth. It will be appreciated, however, that this method may be used in any circumstance where two sensor measurements are taken and the result of one measurement can be used to limit the possible outcomes of the other measurement. The sensed parameter is not limited to pressure but may be any parameter. Further, the wireless sensors 14 and ambient sensor do not necessarily have to measure the same quantity or parameter but may instead measure different quantities or parameters.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

We claim:

1. A wireless sensor reader comprising:
   a transmit circuit configured to generate an excitation pulse to cause a wireless sensor to emit a ring signal;
   an antenna configured to transmit said excitation pulse and receive said ring signal;
   a phase-locked loop circuit configured to receive said ring signal, said phase-locked loop circuit including a voltage-controlled oscillator configured to generate a count signal at a frequency related to said ring signal frequency;
   a circuit for identifying a set of possible frequency values of said ring signal for an individual reading;
   wherein said phase-locked loop circuit is capable of being placed in a sample mode to receive said ring signal and adjust the frequency of said count signal based on the frequency of said ring signal;
   wherein at least one of said transmit circuit, said phase-locked loop circuit, said antenna, and said voltage-controlled oscillator are tunable to the identified set of possible frequency values; and
   further wherein said phase-locked loop circuit is capable of being placed in a hold mode to hold the frequency of said count signal constant for a length of time sufficient to determine the frequency of said count signal.

2. The wireless sensor reader of claim 1, wherein said circuit for identifying said set of possible frequency values is a second sensor that measures a parameter related to the parameter being measured by said wireless sensor.

3. The wireless sensor reader of claim 2, wherein said second sensor is an ambient pressure sensor and said wireless sensor is a blood pressure sensor.

4. The wireless sensor reader of claim 1, wherein said antenna is capable of being tuned to transmit an excitation pulse having a frequency that is selected based on said set of possible frequency values of said ring signal.

5. The wireless sensor reader of claim 1, wherein said antenna is capable of being tuned to receive frequencies in a passband based on said set of possible frequency values.

6. The wireless sensor reader of claim 1, wherein said circuitry for conditioning said received signal comprises filters capable of being tuned to reject frequencies outside of a passband based on said set of possible frequency values.

7. The wireless sensor reader of claim 6, wherein said filters comprise digital conversion circuitry and digital filters.

8. The wireless sensor reader of claim 7, wherein said digital filters comprise averaging a set of discrete samples.

9. The wireless sensor reader of claim 1 further comprising a circuitry for conditioning said received signal, wherein said circuitry for conditioning said received signal includes amplifiers capable of being tuned to reject frequencies outside of a passband based on said subset of said ring signal frequency's possible values.

10. The wireless sensor reader of claim 1, wherein said voltage-controlled oscillator's starting frequency value is selected based on said set of possible frequency values of said ring signal.

11. The wireless sensor reader of claim 1, wherein the circuit for identifying a set of possible frequency values of said ring signal includes an algorithm.

12. A method of reading a remote sensor comprising:
identifying a set of possible frequency values of said remote sensor for an individual reading;
tuning circuits to operate in a passband defined by said set of possible frequency values;
transmitting an excitation pulse to said remote sensor;
receiving a ring signal from said remote sensor in response to said excitation pulse;
amplifying said ring signal;
generating a count signal;
adjusting the frequency of said count signal to match the frequency of said ring signal; and
holding the frequency of said count signal constant for a length of time to determine the frequency of said count signal.

13. The method of claim 12, wherein said identification of a set of possible frequency values of said remote sensor comprises measuring a separate parameter related to the parameter being measured by said wireless sensor.

14. The method of claim 13, wherein said separate parameter is ambient pressure and said parameter being measured by said wireless sensor is intravascular blood pressure.

15. The method of claim 12, wherein said excitation pulse is tuned to a frequency value based on said set of possible frequency values of said remote sensor.

16. The method of claim 12, wherein said ring signal is received by an antenna circuit capable of being tuned to receive frequencies in a passband based on said set of possible frequency values of said remote sensor.

17. The method of claim 12, further comprising the step of filtering said ring signal based on said set of possible frequency values of said remote sensor.

18. The method of claim 12, further comprising rejecting frequencies outside the band represented by said set of possible frequency values of said remote sensor during said amplification of said ring signal.

19. The method of claim 12, wherein said count signal's initial value is selected based on said set of possible frequency values of said remote sensor.

20. The method of claim 12, wherein the range over which said frequency of said count signal may be adjusted is bounded by said set of possible frequency values of said remote sensor.

21. A method of obtaining a measurement from a remote location, the method comprising:
identifying a set of possible frequency values of a wireless sensor for an individual reading;
tuning circuits of a reader to operate in a passband defined by said set of possible frequency values;
transmitting an excitation pulse at only a fixed frequency to said wireless sensor;
receiving a signal from said wireless sensor in response to said excitation pulse;
sampling and holding said received signal to hold the frequency of said received signal constant for a length of time sufficient to ascertain the frequency of said received signal;
and ascertaining the frequency of said received signal;
wherein said wireless sensor is configured to change its resonant frequency in proportion to at least one sensed parameter.

22. The method of claim 21, wherein said identification of a set of possible frequency values of a wireless sensor is derived from a separate measurement related to said measurement obtained from said remote location.

23. The method of claim 22, wherein said separate measurement is ambient pressure and said measurement obtained from said remote location is intravascular blood pressure.

24. The method of claim 21, wherein said fixed frequency of said excitation pulse is selected based on said set of possible frequency values.

25. The method of claim 21, wherein said ring signal is received by an antenna circuit capable of being tuned to receive frequencies in a passband based on said set of possible frequency values of said wireless sensor.

26. The method of claim 21, further comprising the step of filtering said signal from said wireless sensor based on said set of possible frequency values of said wireless sensor.

27. The method of claim 21, wherein the process of ascertaining said frequency of said received signal is influenced by said set of possible frequency values of said wireless sensor.

28. A system for obtaining a measurement from a remote location, said system comprising:
a wireless sensor configured to change its resonant frequency in proportion to at least one sensed parameter;
a reader configured to define a band of resonant frequency values, to optimize itself for operation based on said band, to transmit an excitation pulse at only a fixed frequency to said wireless sensor, to receive a signal from said wireless sensor in response to said excitation pulse, and to sample and hold said received signal constant for a length of time sufficient to ascertain the frequency of said received signal.

29. The system of claim 28, wherein said reader includes a second sensor that measures a parameter related to said at least one sensed parameter to define said band of resonant frequency values.

30. The system of claim 29, wherein said second sensor is an ambient pressure sensor and said at least one sensed parameter is blood pressure.

31. The system of claim 28, wherein said fixed frequency of said excitation pulse is selected based on said band of resonant frequency values.

32. The system of claim 28, wherein said optimization comprises adjusting one or more of the following circuits: transmit antenna, receive antenna, analog filter, digital filter, amplifier, voltage-controlled oscillator.

33. A system for obtaining a measurement from a remote location, said system comprising:
a wireless sensor configured to change its resonant frequency in proportion to at least one sensed parameter;
a handheld, battery-powered reader configured to define a band of resonant frequency values, to optimize itself for operation based on said band, to transmit an excitation pulse at only a fixed frequency to said wireless sensor, to receive a signal from said wireless sensor in response to said excitation pulse, and to hold the frequency of said received signal constant for a length of time sufficient to ascertain the frequency of said received signal.

34. The system of claim 33, wherein said reader includes a second sensor that measures a parameter related to said at least one sensed parameter to define said band of resonant frequency values.

35. The system of claim 34, wherein said second sensor is an ambient pressure sensor and said at least one sensed parameter is blood pressure.

36. The system of claim 33, wherein said fixed frequency of said excitation pulse is selected based on said band of resonant frequency values.

37. The system of claim 33, wherein said optimization comprises adjusting one or more of the following circuits: transmit antenna, receive antenna, analog filter, digital filter, amplifier, voltage-controlled oscillator.

38. A method of obtaining a measurement from a remote location, the method comprising:
defining a range of expected values for said measurement;
optimizing a circuitry to operate within said range of expected values;
transmitting an excitation pulse to a wireless sensor;
receiving a signal from said wireless sensor in response to said excitation pulse;
generating a count signal;
adjusting the frequency of said count signal to match the frequency of said received signal;
holding said frequency of said count signal temporarily constant to ascertain the frequency of said count signal; and
ascertaining the frequency of said count signal wherein said wireless sensor is configured to change its resonant frequency in proportion to at least one sensed parameter.

39. The method of claim 38, wherein said definition of a said range of expected values is obtained by measuring a separate parameter related to said measurement from said remote location.

40. The method of claim 39, wherein said separate parameter is ambient pressure and said measurement from said remote location is blood pressure.

41. The method of claim 38, wherein said optimization of circuitry comprises tuning said excitation pulse to a frequency value based on said range of expected values.

42. The method of claim 38, wherein said optimization of circuitry comprises tuning a receiving antenna circuit to receive frequencies in a passband based on said range of expected values.

43. The method of claim 38, wherein said optimization of circuitry comprises filtering said received signal based on said range of expected values.

44. The method of claim 38, wherein said optimization of circuitry comprises adjusting amplifiers which amplify said received signal, based on said range of expected values.

45. The method of claim 38, wherein said optimization of circuitry comprises selecting said count signal's initial value based on said range of expected values.

46. The method of claim 38, wherein said optimization of circuitry comprises limiting the range over which said frequency of said count signal may be adjusted, based on said range of expected values.

47. The method of claim 38, wherein the process of said ascertaining of said frequency of said count signal is bounded by said range of expected values.

48. The method of claim 47, wherein said bounding of said process comprises taking multiple individual measurements, keeping or discarding measurements based on said range of expected values, and averaging said kept measurements.

49. A wireless sensor reader comprising:
a circuit configured to define a set of all possible values of a wireless sensor's frequency output;
a transmit circuit configured to generate an excitation pulse to cause said wireless sensor to emit a signal having a frequency that is proportionate to at least one sensed parameter;
at least one antenna configured to transmit said excitation pulse and receive said emitted signal;
a first circuit configured to generate a count signal; and
a second circuit configured to adjust the frequency of said count signal to match the frequency of said emitted signal;
wherein said reader is configured to hold said count signal temporarily constant to ascertain said frequency of said count signal.

50. The wireless sensor reader of claim 49, wherein said circuit configured to define said set includes a second sensor that measures a parameter related to the parameter being measured by said wireless sensor.

51. The wireless sensor reader of claim 49, wherein said second sensor is an ambient pressure sensor and said wireless sensor is a blood pressure sensor.

52. The wireless sensor reader of claim 49, wherein said antenna is capable of being reconfigured to transmit an excitation pulse whose frequency is selected based on said set of possible values.

53. The wireless sensor reader of claim 49, wherein said antenna is capable of being reconfigured to receive frequencies in a passband based on said set of possible values.

54. The wireless sensor reader of claim 49, wherein said reader further comprises circuitry for conditioning said received signal, including filters capable of being tuned to reject frequencies outside of a passband based on said set of possible values.

55. The wireless sensor reader of claim 54, wherein said filters includes digital conversion circuitry and digital filters.

56. The wireless sensor reader of claim 55, wherein said digital filters comprise averaging a set of discrete samples.

57. The wireless sensor reader of claim 49, wherein said reader further comprises circuitry for conditioning said received signal, including amplifiers capable of being optimized to amplify frequencies inside of a passband based on said set of possible values.

58. The wireless sensor reader of claim 49, wherein said first circuit selects said count signal's initial frequency value based on said set of possible values.

59. The wireless sensor reader of claim 49, wherein said second circuit optimizes said adjustment of said count signal based on said set of possible values.

* * * * *